(12) United States Patent
Seol et al.

(10) Patent No.: US 9,734,315 B2
(45) Date of Patent: Aug. 15, 2017

(54) WEARABLE TERMINAL

(71) Applicant: LG Electronics Inc., Seoul (KR)

(72) Inventors: Jaehyuk Seol, Seoul (KR); Wonseok Joo, Seoul (KR); Chisang You, Seoul (KR); Soyeon Lee, Seoul (KR); Seungwoo Ryu, Seoul (KR); Hosang Lee, Seoul (KR); Hyengcheul Choi, Seoul (KR); Yohan Lim, Seoul (KR); Yuntaek Jung, Seoul (KR)

(73) Assignee: LG Electronics Inc., Seoul (KR)

( * ) Notice: Subject to any disclaimer, the term of this patent is extended or adjusted under 35 U.S.C. 154(b) by 120 days.

(21) Appl. No.: 14/717,720

(22) Filed: May 20, 2015

(65) Prior Publication Data
US 2016/0063232 A1    Mar. 3, 2016

(30) Foreign Application Priority Data

Sep. 1, 2014 (KR) .................. 10-2014-0115248
Sep. 19, 2014 (KR) .................. 10-2014-0124782

(51) Int. Cl.
G06F 21/32     (2013.01)
G06F 3/038     (2013.01)
G06F 3/0354    (2013.01)
A61B 5/0245    (2006.01)
A61B 5/0452    (2006.01)
(Continued)

(52) U.S. Cl.
CPC ............ *G06F 21/32* (2013.01); *A61B 5/0245* (2013.01); *A61B 5/04525* (2013.01); *A61B 5/117* (2013.01); *A61B 5/681* (2013.01); *G04G 9/0064* (2013.01); *G04G 21/08* (2013.01); *G04R 60/04* (2013.01); *G06F 3/038* (2013.01); *G06F 3/03547* (2013.01); *G06K 9/00885* (2013.01); *H01Q 1/273* (2013.01); *H01Q 7/00* (2013.01); *H01Q 21/28* (2013.01); *A61B 5/742* (2013.01); *H01Q 1/38* (2013.01)

(58) Field of Classification Search
None
See application file for complete search history.

(56) References Cited

U.S. PATENT DOCUMENTS 5,191,891 A    3/1993  Righter
6,685,634 B1 * 2/2004  Fry .................. A61B 5/0002
                                              128/903

(Continued)

FOREIGN PATENT DOCUMENTS

JP         3639966 B2    4/2005

*Primary Examiner* — Brian T Gedeon
(74) *Attorney, Agent, or Firm* — Dentons US LLP

(57) ABSTRACT

There is disclosed a wearable terminal including a main body, a main board provided in the main body, a first touch pad provided in a rear surface of the main body, a flexible board configured to connect the main body and the first touch pad to each other, a band coupled to the main body, wound around a user's wrist to secure the main body to the user's body part, a second touch pad provided in the other surface of one surface contacting with the user's body part when the user wears the band, a flexible board having one end connected to the second touch pad and the other end connected to the main board, and a controller configured to extract an electrocardiogram by measuring a difference of electric potentials of body muscles sensed from the first touch pad and the second touch pad.

19 Claims, 25 Drawing Sheets

(51) Int. Cl.
*A61B 5/117* (2016.01)
*G06K 9/00* (2006.01)
*G04R 60/04* (2013.01)
*H01Q 1/27* (2006.01)
*H01Q 21/28* (2006.01)
*G04G 9/00* (2006.01)
*G04G 21/08* (2010.01)
*H01Q 7/00* (2006.01)
A61B 5/00 (2006.01)
H01Q 1/38 (2006.01)

(56) References Cited

U.S. PATENT DOCUMENTS

| | | |
|---|---|---|
| 9,089,270 B2 * | 7/2015 | Song ............... A61B 5/02438 |
| 2006/0136744 A1 | 6/2006 | Lange |
| 2010/0076331 A1 * | 3/2010 | Chan .................. A61B 5/0006 |
| | | 600/522 |
| 2014/0152516 A1 | 6/2014 | Kim et al. |
| 2014/0203989 A1 | 7/2014 | Jeong et al. |

* cited by examiner

WEARABLE TERMINAL

CROSS-REFERENCE TO RELATED APPLICATIONS

This application claims priority to Korean Patent Application No. 10-2014-0115248 filed on Sep. 1, 2014 and 10-2014-0124782 filed on Sep. 19, 2014 in Korea, the entire contents of which is hereby incorporated by reference in its entirety.

BACKGROUND OF THE DISCLOSURE

Field of the Disclosure

Embodiments of the present disclosure relates to a wearable terminal having an ECG (Electrocardiogram) sensor and two overlapped antennas.

Background of the Disclosure

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As such functions become more diversified, the mobile terminal can support more complicated functions such as capturing images or video, reproducing music or video files, playing games, receiving broadcast signals, and the like. By comprehensively and collectively implementing such functions, the mobile terminal may be embodied in the form of a multimedia player or device.

Considered as personal belongings, diverse designs are applied to hand-carry mobile terminals to express personalities of people who possess the hand-carry mobile terminals.

A mechanical profile of a conventional mobile terminal has a hand-carried size such that a user can carry the mobile terminal in the hand, a bag or a pocket. There is a risk of loss or damage caused by falling, which makes the conventional mobile terminal unhandy to carry about.

To solve the disadvantage, diverse types of wearable terminals are released which can be worn on the wrists as watches, the necks or the waists. Such wearable terminals may have various sizes and functions in accordance with wearing types. Various types of wearable terminals may be used as users' needs arise.

However, the size of such a wearable terminal tends to get smaller, different from a conventional bar or folder type mobile terminal. It is difficult to secure a space for mounting parts in the wearable terminal. Especially, as a device using an electromagnetic wave (e.g., an antenna) is affected by peripheral electronic parts, it is difficult to arrange the electronic parts in the device using the electromagnetic wave.

SUMMARY OF THE DISCLOSURE

Accordingly, an object of the present invention is to address the above-noted and other problems.

An object of the present disclosure is to provide a wearable terminal including an ECG sensor to be controlled based on presence of user authentication.

Embodiments of the present disclosure may provide a wearable terminal including a main body; a main board provided in the main body; a first touch pad provided in a rear surface of the main body; a flexible board configured to connect the main body and the first touch pad to each other; a band coupled to the main body, wound around a user's wrist to secure the main body to the user's body part; a second touch pad provided in the other surface of one surface contacting with the user's body part when the user wears the band; a flexible board having one end connected to the second touch pad and the other end connected to the main board; and a controller configured to extract an electrocardiogram by measuring a difference of electric potentials of body muscles sensed from the first touch pad and the second touch pad.

The band may include a lower band configured to contact with the user's body part; an upper band coupled to the lower band, having the flexible board mounted therein, and the upper band may include a hole to which the second touch pad is coupled.

The wearable terminal may further include a conductive elastic material disposed between the second touch pad and the flexible board to electrically connect the second touch pad and the flexible board to each other.

The wearable terminal may further include a middle band disposed between the upper band and the flexible board, with a thickness corresponding to the thickness of the conductive elastic material.

The band may include a first band coupled to one side of the main body, with one end in which a buckle is formed; and a second band coupled to the other side of the main body, with one end in which the second touch pad is provided, and the second band comprises a plurality of holes formed along a longitudinal direction, and the flexible board may have omitted areas corresponding to the holes.

The wearable terminal may further include an antenna formed in the other area of the flexible board.

The controller may convert an idle screen into a basic screen when sensing a difference of electric potentials from the first touch pad.

The controller measures the user's electrocardiogram when change in electric potentials is sensed from the first touch pad and the second touch pad. The controller may perform user authentication by comparing the measured electrocardiogram with a designated user's electrocardiogram.

When the designated user's preset electrocardiogram is matched up with the user's electrocardiogram, a function preset by the designated user may be implemented or the function may be expanded.

The expanded function may include one or more of controlling of an external device when the user approaches the wearable terminal near the external device, an external device implementing user authentication, and controlling of a designated external device when a control command is inputted are performed.

The expanded function may be a payment function.

The identified user authentication may be canceled when the contact status of the first touch pad is released.

A guide for the user authentication may be provided when the user authentication fails.

Location information of the wearable terminal may be sent to a server or an alarm may be sent to a predesignated opponent, when the user authentication fails n times.

The wearable terminal may further include an antenna module connected to the main board to permit transmission/reception of a signal, wherein the antenna module may include a first antenna comprising a first radiation unit formed in a spiral form; and a second antenna disposed on the first antenna, with an area overlapped with the first radiation unit which occupies 25% or less of an overall area.

The first antenna may include a first insulation sheet; a first radiation unit formed on the first insulation sheet, in a spiral form; a first connection unit extending from an end provided an outer area from the spiral form of the first radiation unit, to be connected to the main board; and a second connection unit extending from one end provided in an inner area from the spiral form of the first radiation unit to be connected to the main board, partially overlapped with the radiation unit, and the overlapped area between the second connection unit and the first radiation unit may be provided in one surface and the other surface of the first insulation sheet, respectively.

The main board may further include a power feeding unit connected to the power supply unit to supply a power to the first radiation unit; and a high frequency reject module disposed between the power feeding unit and one or more of the first and second connection units.

The high frequency reject module may include one or more of a low pass filter configured to pass only the low frequency there through, a low band pass filter configured to pass only a signal corresponding to a frequency in a preset low frequency band there through, a high reject filter and a high reject filter configured to reflect a signal corresponding to a preset high frequency band.

The high frequency reject module may include one or more of combination of inductor and capacitor, a ceramic/dielectric filter, SAW (surface acoustic wave), MEMS (micro electro mechanical systems), LTCC (Low Temperature Co-firing Ceramics) and FBAR (Film Bulk Acoustic Resonator).

The second antenna may include a second insulation sheet; a second radiation unit formed on the second insulation sheet in a loop shape, located around a first radiation unit; and a third connection unit connected to the second radiation unit to be connected to the main board.

The second antenna may include a second insulation sheet; a third connection unit connected to the second radiation unit to be connected to the main board; and a second radiation unit formed in a loop shape, around the first radiation unit or a bar shape extending from the third connection unit into the first radiation unit, partially overlapped with the first radiation unit.

The main board may further include a power feeding unit connected to the power supply unit to supply a power to the second radiation unit; and a low frequency reject module disposed between the power feeding unit and the third connection unit.

The low frequency reject module may include one or more of a low pass filter configured to pass only the low frequency there through, a low band pass filter configured to pass only a signal corresponding to a frequency in a preset low frequency band there through, a high reject filter and a high reject filter configured to reflect a signal corresponding to a preset high frequency band.

The low frequency reject module may include one or more of combination of inductor and capacitor, a ceramic/dielectric filter, SAW (surface acoustic wave), MEMS (micro electro mechanical systems), LTCC (Low Temperature Co-firing Ceramics) and FBAR (Film Bulk Acoustic Resonator).

The wearable terminal may further include a protection film disposed on one or more of exposed surfaces of the first and second antennas.

The first radiation unit may be a NFC (Near Field Communication) antenna and the second radiation unit is a MIMO (Multiple Input Multiple Output) antenna.

The first radiation unit may be a low frequency antenna configured to send/receive a signal in a frequency band of 20 MHz or less and the second radiation unit is a high frequency antenna configured to send/receive a signal in frequency band between 700 MHz or more and 1.7 GHz or less.

The wearable terminal may further include a third radiation unit formed on the first antenna to prevent the first and second radiation units from being overlapped with each other.

The wearable terminal may further include a band coupled to both ends of the main body, wound around a user's wrist to secure the main body to the user's body part, wherein the antenna module is mounted in the band, formed of a flexible material.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings, which are given by illustration only, and thus are not limitative of the present invention, and wherein.

DESCRIPTION OF SPECIFIC EMBODIMENTS

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Figure 1:
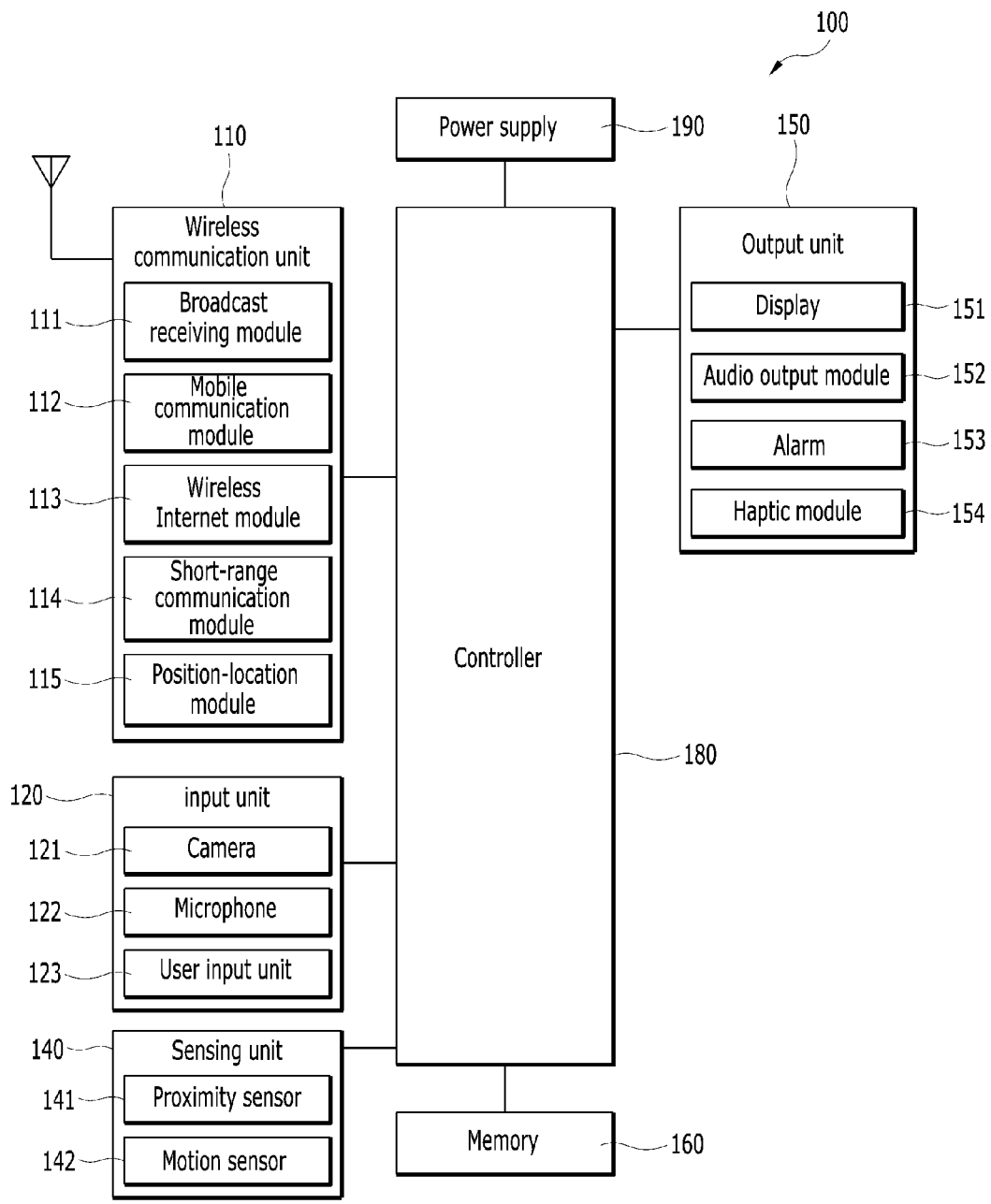
FIG. 1 is a block diagram illustrating a wearable terminal in accordance with the present disclosure.

FIG. 1 is a block diagram of a mobile terminal in accordance with the present disclosure.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Referring now to FIG. 1, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs.

The controller 180 may provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

A typical wearable device can exchange data with (or cooperate with) another mobile terminal 100. In such a device, the wearable device generally has functionality that is less than the cooperating mobile terminal. For instance, the short-range communication module 114 of a mobile terminal 100 may sense or recognize a wearable device that is near-enough to communicate with the mobile terminal. In addition, when the sensed wearable device is a device which is authenticated to communicate with the mobile terminal 100, the controller 180 may transmit data processed in the mobile terminal 100 to the wearable device via the short-range communication module 114, for example. Hence, a user of the wearable device can use the data processed in the mobile terminal 100 on the wearable device. For example, when a call is received in the mobile terminal 100, the user can answer the call using the wearable device. Also, when a message is received in the mobile terminal 100, the user can check the received message using the wearable device.

Short-range wireless communication permits exchange of data with a near-enough external terminal and uses a low frequency which is transmitted close to the ground, not spread in the air. An antenna for short-range wireless communication may be referred to as a low frequency antenna.

To function as an independent terminal itself, the wearable terminal has to facilitate long-range wireless communication which permits direct communication with a radio base station as well as the short-range wireless communication. Examples of such long-distance wireless communication include GSM (Global System for Mobile communication), CDMA (Code Division Multi Access), CDMA2000 (Code Division Multi Access 2000), EV-DO (Enhanced Voice-Data Optimized or Enhanced Voice-Data Only), WCDMA (Wideband CDMA), HSDPA (High Speed Downlink Packet Access), HSUPA (High Speed Uplink Packet Access), LTE (Long Term Evolution) and LTE-A (Long Term Evolution-Advanced). The long-range wireless communication permits a wireless signal received and sent or to one or more of a base station, an external terminal and a server on a mobile communication network established according to corresponding wireless communication standards.

Such the long-range wireless communication uses signals in a high frequency band which has a strong linearity and an antenna for the long-range wireless communication can be referenced to as a high frequency antenna.

Embodiments of the present disclosure provide a wearable terminal having a high frequency antenna as well as the low frequency antenna mentioned above mounted therein. Examples of the wearable terminal 100 include a start watch, a smart glass, a HMD (a head mounted display) and the like. Various wearable terminals are adopted to describe the embodiments of the present disclosure and a smart watch among the examples is applied.

Figure 2:
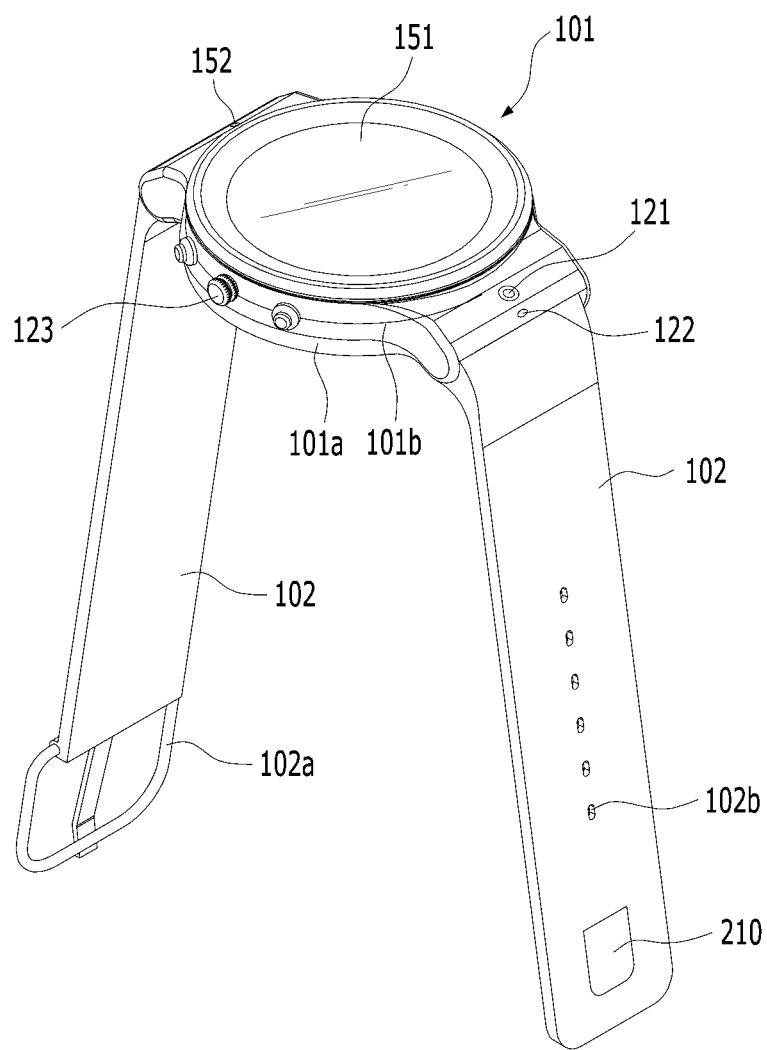
FIG. 2 is a perspective diagram illustrating a wearable terminal in accordance with one embodiment of the present disclosure.

FIG. 2 is a perspective view illustrating one example of a watch-type mobile terminal 100 in accordance with another exemplary embodiment.

In the embodiment, a watch-type mobile terminal 100 as the wearable terminal includes a main body 101 having a display unit 151 and a band 102 connected to the main body 101 to be wearable on a user's wrist.

The main body 101 may include a case having a certain appearance. As illustrated, the case may include a first case 101*a* and a second case 101*b* cooperatively defining an inner space for accommodating various electronic components for example main substrate 185, camera 121, Audio output module 152. For instance, a single case may alternatively be implemented, with such a case being configured to define the inner space, thereby implementing a mobile terminal 100 with a uni-body.

The watch-type mobile terminal 100 can perform wireless communication, and an antenna for the wireless communication can be installed in the main body 101. The antenna may extend its function using the case. For example, a case including a conductive material may be electrically connected to the antenna to extend a ground area or a radiation area.

The display unit 151 is shown located at the front side of the main body 101 so that displayed information is viewable to a user. In some embodiments, the display unit 151 includes a touch sensor so that the display unit can function as a touch screen. As illustrated, window 151*a* is positioned on the first case 101*a* to form a front surface of the terminal body together with the first case 101*a*.

The illustrated embodiment includes audio output module 152, a camera 121, a microphone 122, and a user input unit 123 positioned on the main body 101. When the display unit 151 is implemented as a touch screen, additional function keys may be minimized or eliminated. For example, when the touch screen is implemented, the user input unit 123 may be omitted.

The band 102 is commonly worn on the user's wrist and may be made of a flexible material for facilitating wearing of the device. As one example, the band 102 may be made of fur, rubber, silicon, synthetic resin, or the like. The band 102 may also be configured to be detachable from the main body 101. Accordingly, the band 102 may be replaceable with various types of bands according to a user's preference.

In one configuration, the band 102 may be used for extending the performance of the antenna. For example, the band may include therein a ground extending portion (not shown) electrically connected to the antenna to extend a ground area.

The band 102 may include fastener 102*a*. The fastener 102*a* may be implemented into a buckle type, a snap-fit hook structure, a Velcro® type, or the like, and include a flexible section or material. The drawing illustrates an example that the fastener 102*a* is implemented using a buckle.

When the band 102 includes a buckle type fastener 102*a*, a hole 102*b* may be formed in the other opposite area of the band 102 to a buckle fixing pin therein.

As a unique feature or characteristic of the present disclosure, the watch-type terminal may include an ECG (Electrocardiogram) sensor 145. An electrocardiogram records as graphs electric potential associated with heart contraction or electrical activity in a person's heart that has the electrocardiogram. An electrocardiogram measuring device typically used in a hospital measures an electrocardiogram by recording electric potentials in 12 physical areas, using 12 electrons.

The electrocardiogram is used in diagnosis of cardiovascular diseases, for example, arrhythmia and coronary artery. Inspection equipment, for example, an echocardiographic assessment, CT, MRI and the like may be used in such diagnosis. However, such inspection equipment has a defect of high cost. Especially, the electrocardiogram is useful in monitoring a cardiac patient's condition and permits passage observation through continuous electrocardiogram measurement.

As each person has a unique cardiac activity pattern, the electrocardiogram extends its function of identifying a user from the function of simply measuring the cardiac diseases. When the wearable terminal 100 includes the ECG sensor, the user's electrocardiogram can be measurable frequently. The wearable terminal 100 including the ECG sensor 145 may be used as biometric authentication for identifying the user based on comparison with a unique cardiac pattern for each person.

The electrocardiogram sensor 145 provided in the wearable terminal 100 in accordance with the present disclosure measures electric potentials of the user's left and right hands, using two touch pads, so as to measure the user's electrocardiogram. A first touch pad 200 measures an electric potential of the hand on which the wearable terminal 100 is worn and a second touch pad 210 measures an electric potential of the other hand.

Figure 3:
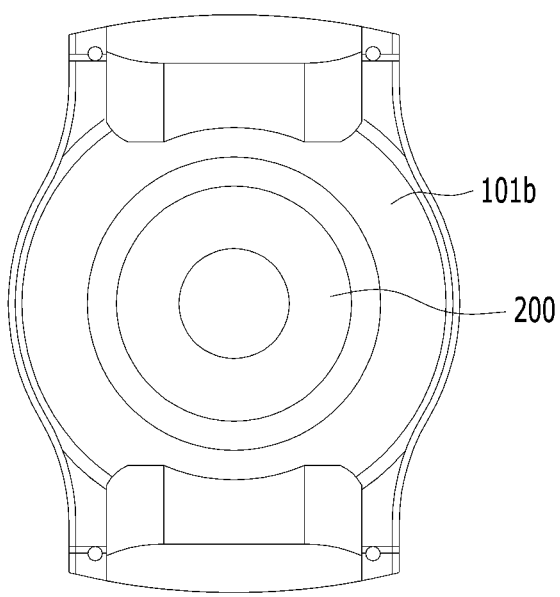
FIG. 3 is a rear view illustrating the wearable terminal in accordance with one embodiment of the present disclosure.

FIG. 3 is a rear view illustrating the main body 101 provided in the wearable terminal 100 in accordance with one embodiment of the present disclosure. The first touch pad 200 shown in FIG. 3 is provided in a rear surface of the main body 100 composing the wearable terminal 100, in other words, an area in contact with the user's body part when the wearable terminal 100 is worn on the user's body part. The second touch pad 210 shown in FIG. 2 may be provided in an outer surface of the band provided in the wearable terminal 100, in other words, the other surface of the body touching surface when the wearable terminal 100 is worn on the user's body part.

Figure 4:
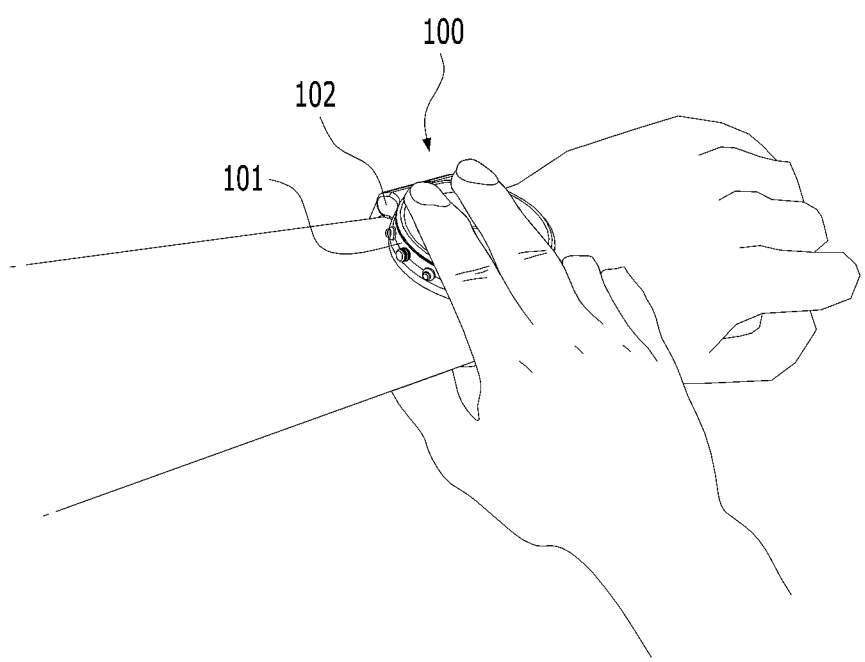
FIG. 4 is a diagram illustrating a method of measuring ECG in accordance with one embodiment of the wearable terminal.

When the user wears the wearable terminal 100 on the hand, the first touch pad 200 touches the hand and the second touch pad 210 is exposed outside. When the user holds the wearable terminal 100 in the hand not wearable terminal 100 as shown in FIG. 4, the hand having the wearable terminal 100 is in close contact with the first touch pad 200 and the second touch pad 210 is in contact with the thumb of the other hand without the wearable terminal 100. As the user's body parts contact with the two touch pads 200 and 210, respectively, the ECG sensor may measure electric potentials of the hands and thereby measure the user's electrocardiogram.

Figure 5:
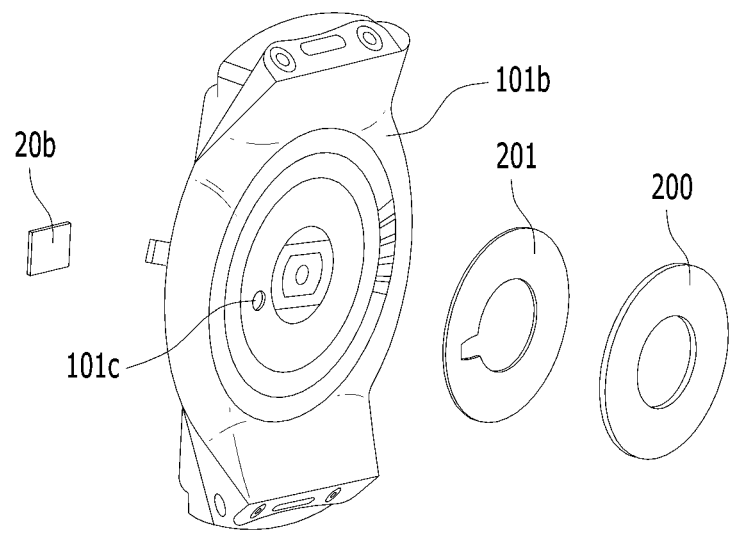
FIG. 5 is an exploded perspective diagram of a main body provided in the wearable terminal in accordance with one embodiment of the present disclosure.
Figure 6:
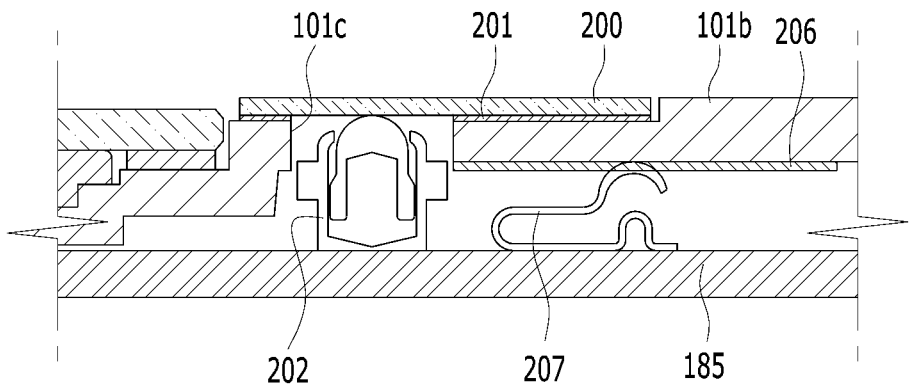
FIG. 6 is a sectional diagram of a main body provided in the wearable terminal in accordance with one embodiment of the present disclosure.

FIG. 5 is an exploded perspective diagram of FIG. 3 and FIG. 6 is a sectional diagram of FIG. 3. The first touch pad 200 provided in the rear surface of the main body 101 may be coupled to a rear surface of the rear case 101*b*, using a double-sided tape 201. As illustrated, the first touch pad 200 is donut-shaped and the shape of the first touch pad is not limited thereto. The shape of the first touch pad 200 may be rectangular or circular.

To connect the first touch pad 200 to a main board 185 provided in the main body, a pogo pin 202 shown in FIG. 6 may be used or an elastic terminal, for example, a C-clip may be used.

A copper sheet 206 for grounding may be further provided in an inner surface of the rear case 101*b*. To connect the copper sheet 206 as a ground plane to the main board 185, a C-clip 207 which is an elastic terminal may be provided. Once grounded, the accuracy of the electric potential measured in the first touch pad 200 can be improved.

Figure 7:
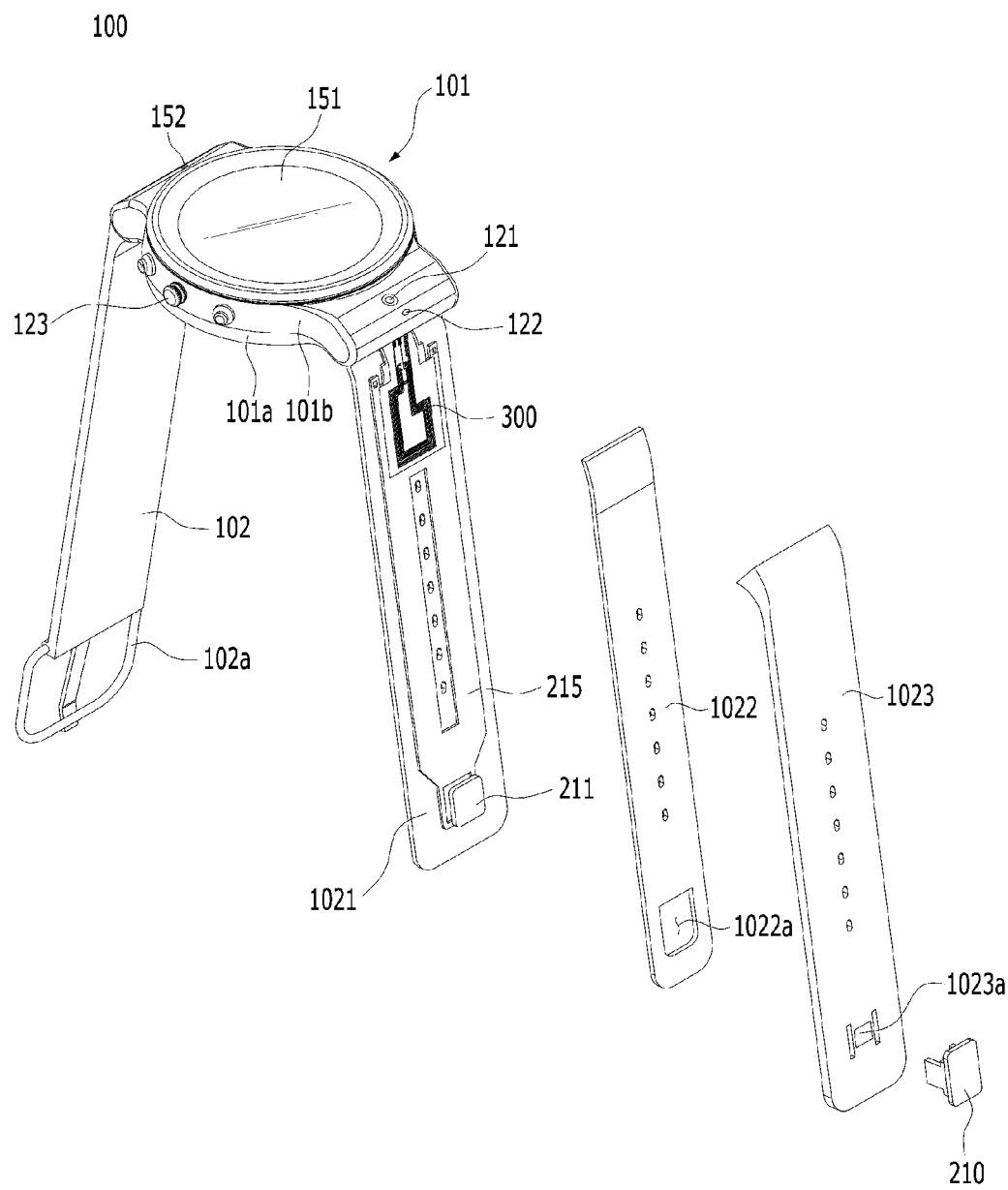
FIG. 7 is an exploded perspective diagram of a band provided in the wearable terminal in accordance with one embodiment of the present disclosure.
Figure 8:
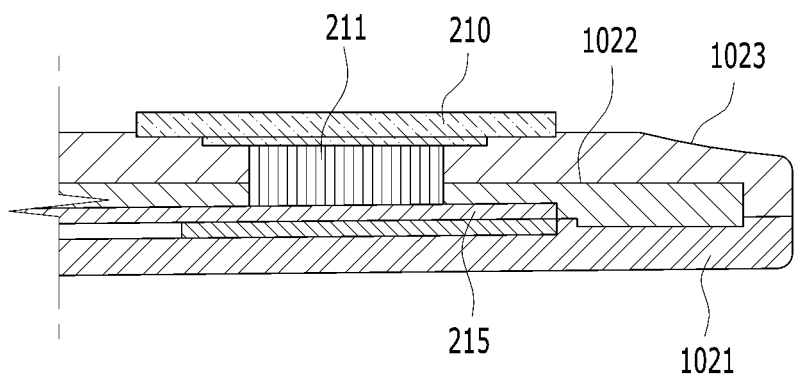
FIG. 8 is a sectional diagram of a band provided in the wearable terminal in accordance with one embodiment of the present disclosure.

FIG. 7 is an exploded perspective diagram of a band provided in the wearable terminal 100 in accordance with one embodiment of the present disclosure. FIG. 8 is a sectional diagram of the band provided in the wearable terminal 100 in accordance with one embodiment of the present disclosure. The band may include a lower band 1021 contacting with the user's body part and an upper band 1023 coupled to the lower band 1021, with the flexible board 215 disposed therein.

The band may further include a middle band 1022 configured to compensate heights of components mounted between the lower band 1021 and the upper band 1023 and to protect the internal components. The band 102 may be formed of a flexible material so that it can be wound around the user's wrist. The flexible board 215 mounted in the band 102 may be also formed of a flexible material.

The second touch pad 210 may be provided on an outer surface of the band, in other words, a surface not touched with the user's body part. The second touch pad 210 may be connected to the flexible board 215. The electric potentials of the user's body part collected in the second touch pad 210 may be transmitted to the main board 185 via the flexible board 215.

The antennal module 300 may be provided in the band of the watch-type terminal as the wearable terminal. In the embodiment, the antenna module 300 located in the band is described. However, the antenna module 300 may be alternatively mounted in the main body 101.

In case mounted in the band 102, the antenna module 300 may be provided adjacent to the main body 101. When the band 102 is formed of a flexible material to be freely wound around the user's wrist, the antenna module 300 is also formed of a flexible material.

The antenna module 300 will be described in detail later.
As shown in FIG. 8, the second touch pad 210 and the flexible board 215 are spaced apart from each other by the upper band and the middle band, so that a conductive elastic material 211 may be disposed between the upper band and the middle band. If a hard material such as metal is disposed, connection efficiency might deteriorate in bending the band 102. A flexible material with conductivity, for example, Gore-Tex is used and then a connected state is maintained even when the band is bent. After that, the band can be restituted.

The flexible board 215 is not necessarily provided in an entire area of the band and it is required to be provided in an area which is as wide as a signal line between the main board 185 and the second touch pad 210 can be arranged accordingly, as shown in FIG. 7, the flexible board 215 may be provided only in both side areas of the hole 102b, except an area corresponding to the hole 102b having a buckle pin of the buckle 102a inserted therein. The second touch pad 210 is provided in a predetermined area of the flexible board 215 and the other components such as an antenna shown in FIG. 7 may be mounted in the other area of the flexible board 215.

Using the ECG (Electrocardiogram) sensor 145 having the structure mentioned above, the electrocardiogram is measured so that the user's physical condition can be measured and a personalized function for each user can be provided based on information on the user's unique electrocardiogram.

Figure 9:
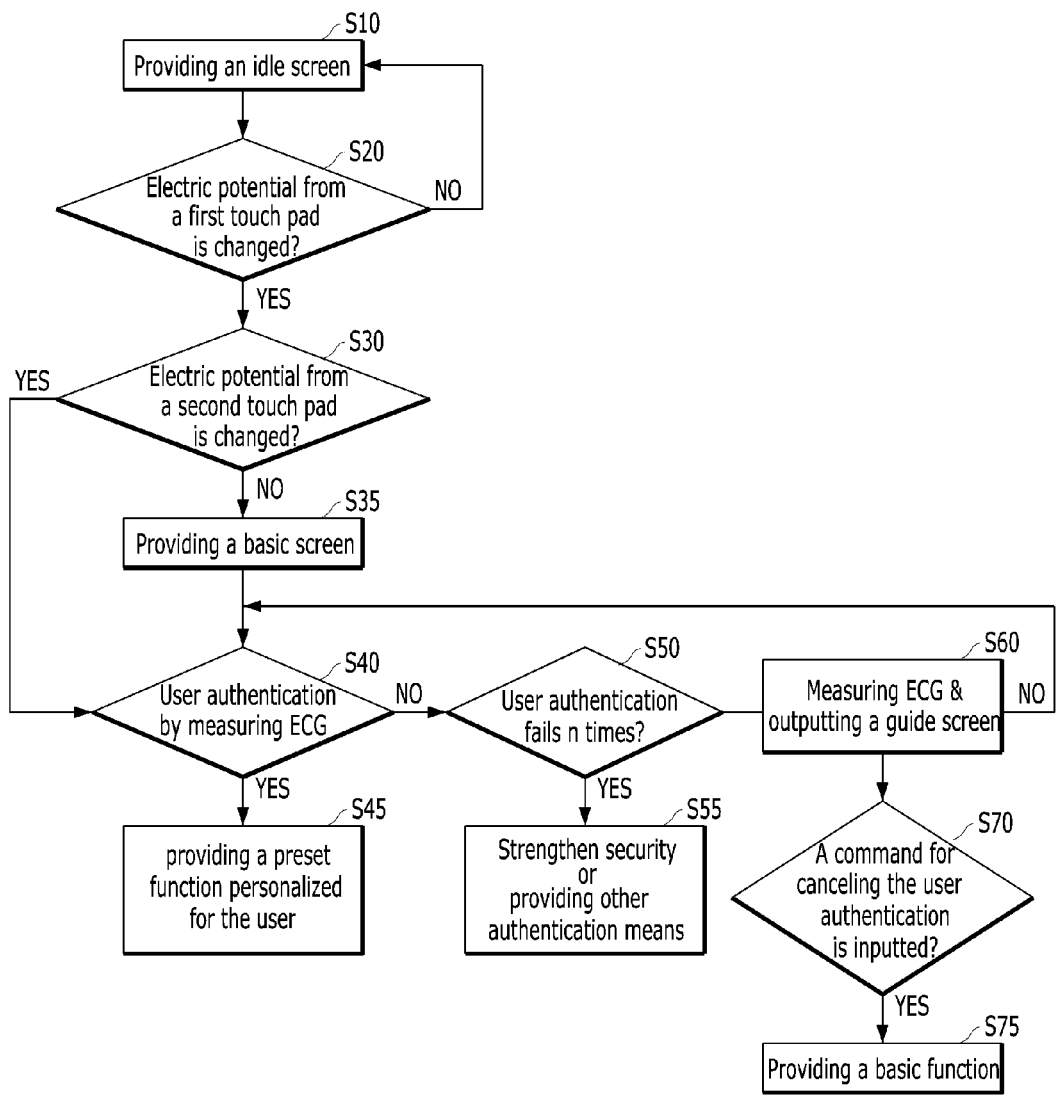
FIG. 9 is a flow chart illustrating a method of measuring ECG and controlling the wearable terminal in accordance with one embodiment of the present disclosure.

FIG. 9 is a flow chart illustrating a method of measuring ECG and controlling the wearable terminal 100 in accordance with one embodiment of the present disclosure. FIGS. 10 through 13 are diagrams illustrating a screen of a display unit 151 to explain a usage example of the wearable terminal 100 shown in FIG. 9.

Figure 10A:
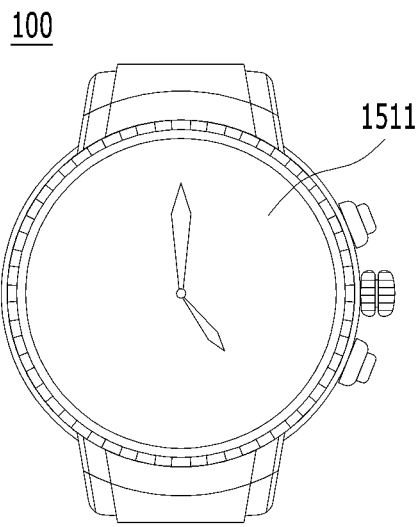
FIGS. 10(a) and 10(b) are diagrams illustrating a screen of a display unit to explain a usage example of the wearable terminal shown in FIG. 9.

Before the user wears the wearable terminal 100, an idle screen 1511 is provided (S10). The idle screen 1511 may be in a state where the display unit 151 is turned off and it may be a clock screen displaying time information through the display unit 151 as shown in FIG. 10(a).

Figure 10B:
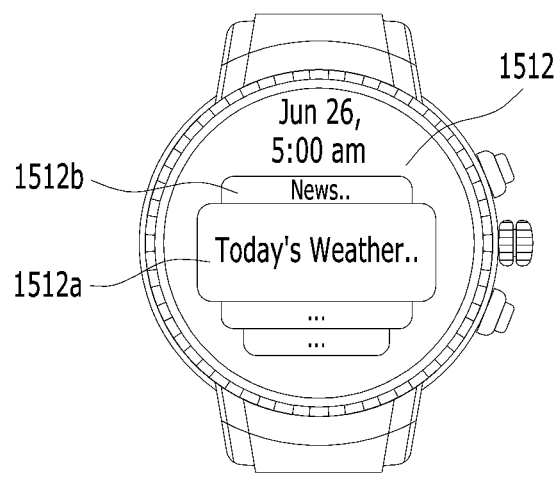

It is determined that the user wears the wearable terminal 100 when change in electric potentials is sensed only from the first touch pad 200 in the idle screen 1511 (S20). Once it is determined that the user wears the wearable terminal, a basic screen 1512 shown in FIG. 10(b) is provided (S30). The basic screen 1512 is provided, regardless of the user, and it provides a graphic user interface to permit the user to use basic functions. Examples of the basic functions include weather information checking 1512a, news reading 1512b, time information checking, call placing, photographing and internet using. Checking of a contact list for each user or received messages or viewing of pictures may be limited.

When change in electric potentials measured from the second touch pad 210 is sensed, the electrocardiogram is measured and user authentication is processed (S40). Electric potential change is sensed from the first touch pad 200 and the second touch pad 210 in a state where the user is holding the wearable terminal 100 as shown in FIG. 4.

Figure 11:
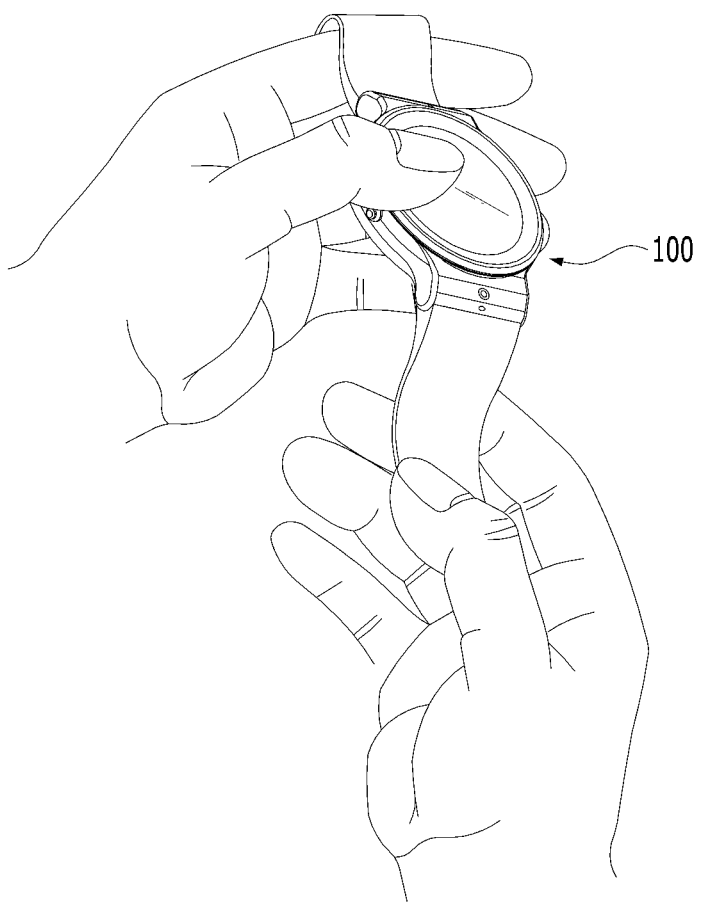
FIG. 11 is a diagram illustrating a screen of a display unit to explain a usage example of the wearable terminal shown in FIG. 9.

Alternatively, the cardiogram is measured and user authentication is processed (S40), when electric potential change is sensed from the first touch pad 200 and the second touch pad 210 even in a state where the user is not wearing the wearable terminal 100 as shown in FIGS. 11 (S20 and S30). Even in a state where the user is holding the wearable terminal 100 as shown in FIG. 11, the user authentication (S40) can be implemented or performed without providing the basic screen.

In a preset time period when the user takes off or does not use the wearable terminal 100 worn by the user after the user authentication is processed, the user authentication is canceled and the current state is converted into a locked state. The user authentication processed state is not ended right after the user takes off the wearable terminal 100 but in a preset time period after the user takes off the wearable terminal 100, only to improve use convenience.

Figure 12A:
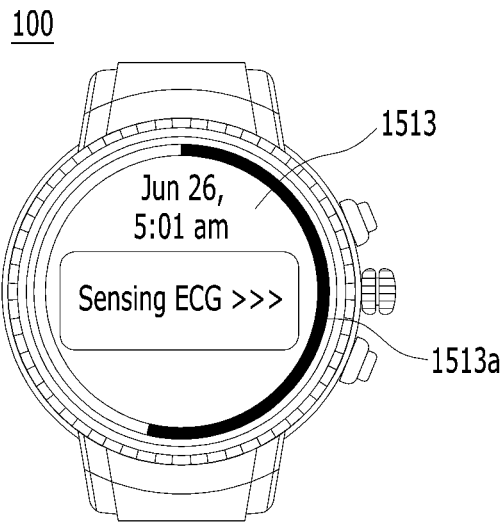
FIGS. 12(a) and 12(b) are diagrams illustrating a screen of a display unit to explain a usage example of the wearable terminal shown in FIG. 9.
Figure 12B:
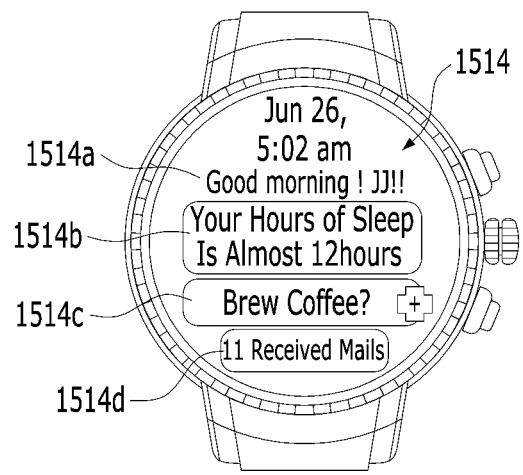

An ongoing state for measuring the electrocardiogram 1513a may be displayed (see FIG. 12(a)). The measured electrocardiogram is matched up with preset information on the user electrocardiogram, a preset function personalized for the user or a user interface 1514 may be provided (S45). FIG. 12(b) illustrates one example of a screen 1514 after the user authentication process using the ECG sensor 145. The user's name is displayed (1514a) to check the authenticated user.

Alternatively, the user's sleeping hours are measured and displayed (1514b) or messages received during the night are displayed (S1514d), so that the user can be provided with the information collected or received while the wearable terminal 100 is not used via the display unit 151 or the auto output unit 152.

Functions personalized according to the user's life pattern may be provided based on user input information and use log. For instance, a user interface 1514a may be provided to ask whether to operate a coffee machine at a preset time set as a coffee time or in case there are records of using the coffee machine in the morning.

In case there are mostly log records for checking news, it is asked whether to provide news. Contents of schedules on the day may be provided to the user who periodically checks a scheduler.

User personalized extension functions may provide a function or graphic user interface set by the user. Functions used by the user often based on the time are analyzed so that graphic user interfaces appropriate to the analyzed functions may be displayed on the screen or appropriate functions can be implemented.

Figure 13A:
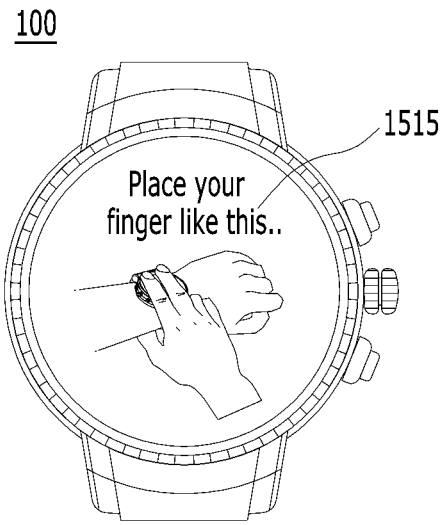
FIGS. 13(a) and 13(b) are diagrams illustrating a screen of a display unit to explain a usage example of the wearable terminal shown in FIG. 9.
Figure 13B:
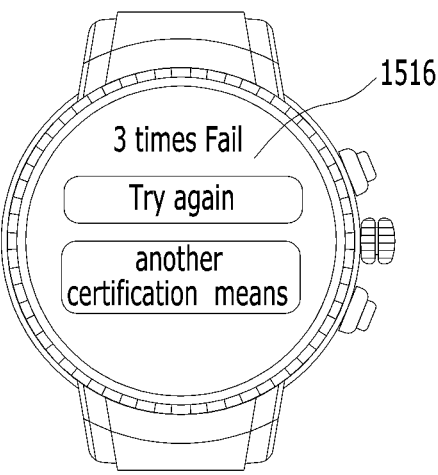

In case user authentication based on ECG measuring failed shown in FIG. 13, a guide screen 1515 guiding the user to place his or her hand in an accurate position may be output on the display unit 151 or a guide voice may be provided via the audio output unit 152. Using characters, voices or images, the position of the hand may be guided to contact with the first touch pad 200 and the second touch pad 210 closely so as to measure the ECG accurately (S60).

However, when the user authentication failed n times or more (S50), it is determined that a third person, not the registered user, tries authentication and security is strengthened (S55). In this instance, other identification means, for example, inputting a password, a personal identification number or a unlock pattern may be provided to implement the user authentication (1516).

Figure 14A:
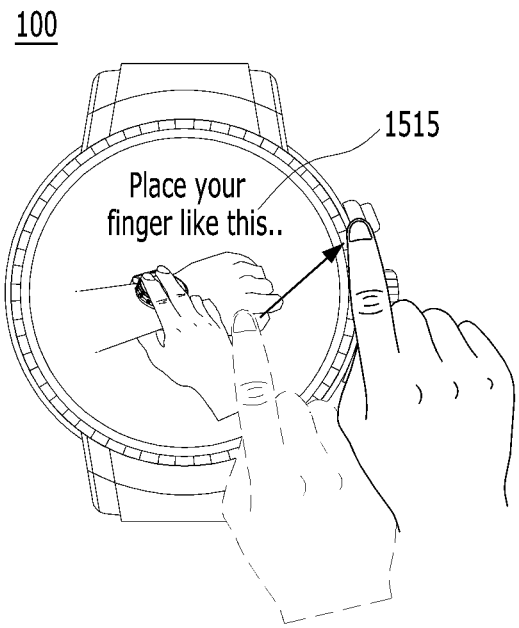
FIGS. 14(a) and 14(b) are diagrams illustrating a method of ending ECG measurement in the wearable terminal accordance with one embodiment of the present disclosure.
Figure 14B:
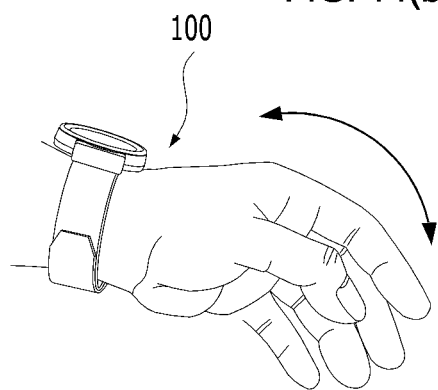

ECG measuring may be ended freely as shown in FIG. 14 to allow the terminal without the user authentication. When a guide screen for is displayed to re-measure the ECG after the user authentication failed, the user authentication can be ended by inputting a specific touch pattern as shown in FIG. 14(*a*). Alternatively, the user authentication may be ended by inputting a specific gesture as shown in FIG. 14(*b*).

When the user authentication is canceled as shown in FIGS. 14(*a*) and (*b*), the current screen is changed into the basic screen 1512 (see FIG. 10(*a*)) or the idle screen 1511 (see FIG. 10(*b*)).

Figure 15A:
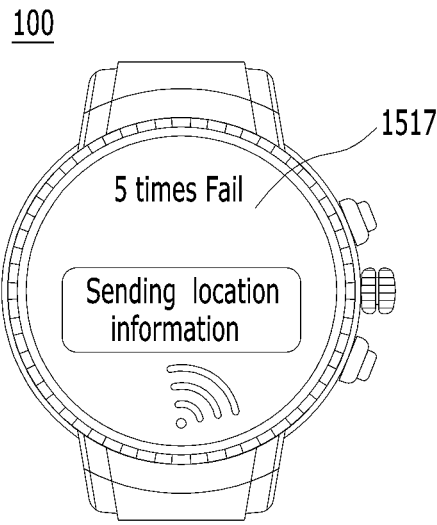
FIGS. 15(a) and 15(b) are diagrams illustrating a method of ending ECG measurement in the wearable terminal accordance with one embodiment of the present disclosure.
Figure 15B:
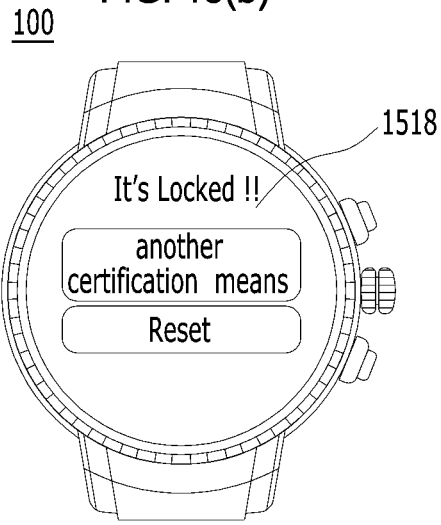

In case it is determined that the wearable terminal is lost or stolen as shown in FIG. 15(*a*), information on a location of the wearable terminal is sent to the server to locate the lost or stolen wearable terminal 100. The user can send the location information to a designated person or opponent or place a call to the designated person or opponent (1517).

Alternatively, security is strengthened as shown in FIG. 15(*b*) so that the wearable terminal 100 may be controlled to be used only through double locking or security-strengthened user identification means for the user authentication to permit the user to use a plurality of means for the user authentication.

Figure 16A:
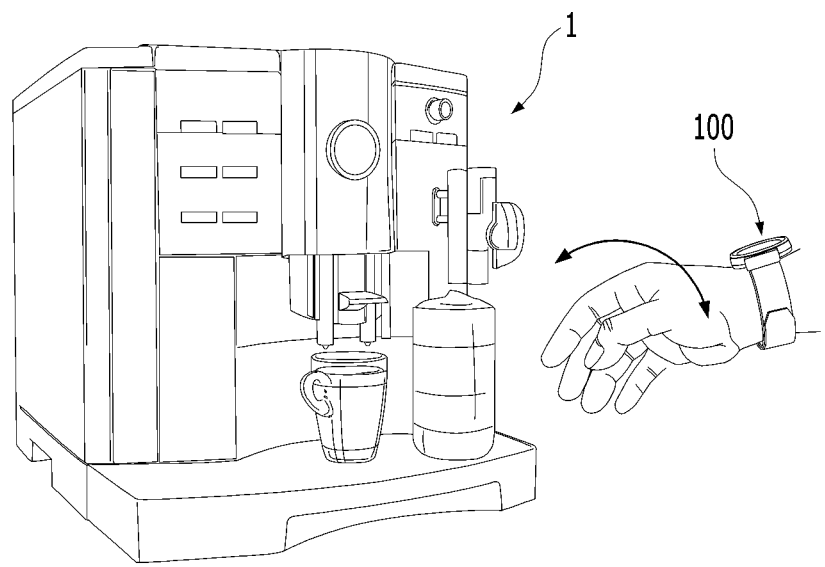
FIGS. 16(a) and 16(b) are diagrams illustrating personalized control for a user of the wearable terminal in accordance with the present disclosure.
Figure 16B:
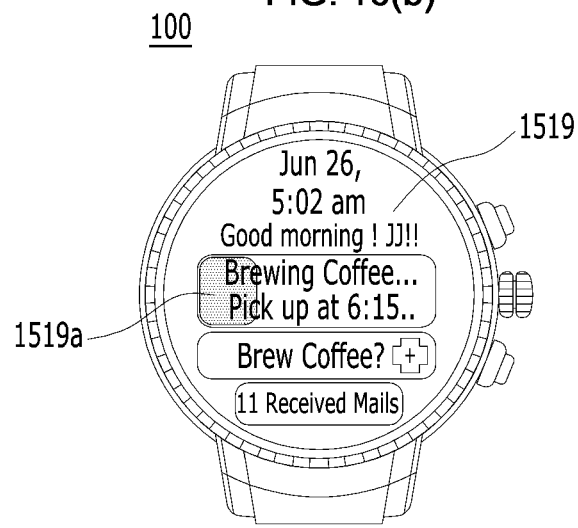
Figure 17A:
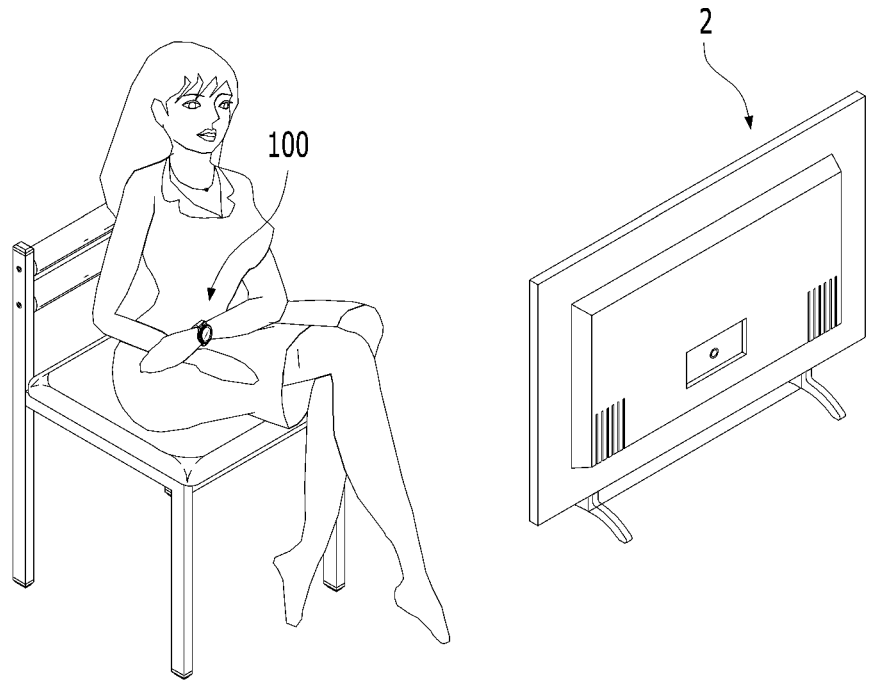
FIGS. 17(a) and 17(b) are diagrams illustrating personalized control for a user of the wearable terminal in accordance with the present disclosure.
Figure 17B:
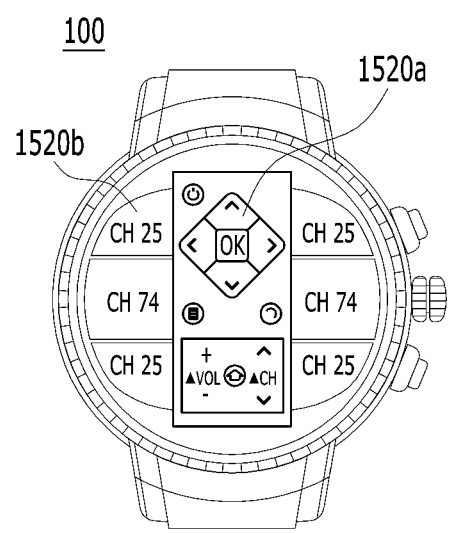
Figure 18A:
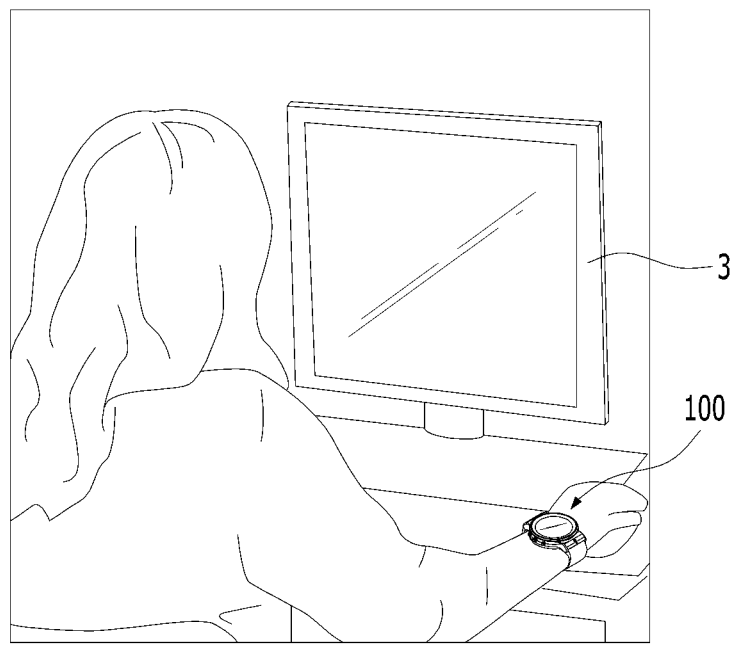
FIGS. 18(a) and 18(b) are diagrams illustrating personalized control for a user of the wearable terminal in accordance with the present disclosure.
Figure 18B:
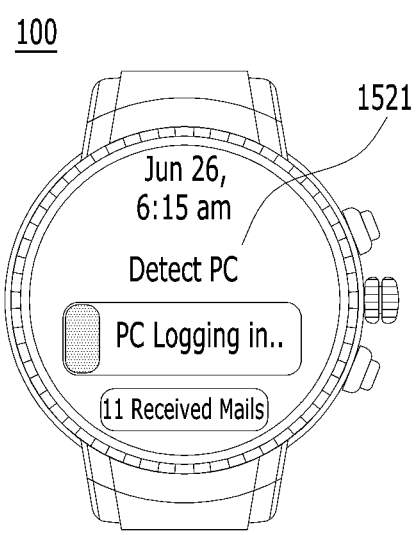

FIGS. 16 through 18 are diagrams illustrating personalized control for a user of the wearable terminal in accordance with the present disclosure. Once the user authentication is completed, using the ECG sensor 145, a user command can be inputted to the wearable terminal 100 in a manners set by the user.

For instance, when the user inputs a specific gesture made by moving the hand wearing the wearable terminal 100 as shown in FIG. 16, a function corresponding to the gesture may be performed or implemented. Examples of the gestures shown in FIG. 16(*a*) may include a hand shaking gesture by rotating the wrist, a knocking gesture, an arm piling gesture and a clapping gesture.

The wearable terminal 100 may be controlled via wireless communication with a near-enough external device. For instance, the near-enough external device may be a home electric appliance (e.g., a washing machine, a coffee machine 1 and a TV 2) and a desktop computer 3. When the wearable terminal 100 approaches the external device, it is determined that the user desires to use the corresponding external device so that a menu configured to control the corresponding external device or information on the corresponding external device may be output.

When the wearable terminal 100 approaches the coffee machine 1, a graphic user interface configured to ask whether to brew coffee may be provided and the user may then input a control command for brewing coffee may be input on the corresponding graphic user interface or the user may input the control command by a preset gesture shown in FIG. 14(*a*).

In case a preset gesture is sensed before communication with a near-enough external device is connected, it is searched whether there is a record of an external device controlled by the corresponding gesture. When there is the record, it is sensed whether the corresponding external device is nearby and wireless communication is tried. A command corresponding to the gesture is transmitted to the external device to control the external device.

Accordingly, the user may be provided with the information on the state of the external device via wireless communication between the external device and the wearable terminal 100. As shown in FIG. 16(*b*), a process 1519*a* of extracting information may be displayed on the display unit. At this time, a type, concentration and quantity of coffee, preferred by the user may be adjusted before coffee is provided.

Once the coffee extraction is ended, the external device identifies the user inputting the command for extracting the coffee via the wireless communication with the wearable terminal and permits the user to take the extracted coffee out the coffee machine. As another example, when laundry is washed in the washing machine, the wearable terminal identifies whether the user inputs a command for washing the laundry to permit the user to unload the washed laundry.

FIG. 17 is a diagram illustrating TV control via the wearable terminal 100 when the user is located in front of a TV as another example. When the user approaches the TV as shown in FIG. 15(*a*), a remote control graphic user interface 1520*a* configured to control the TV may be provided (see, FIG. 15(*b*)). Rather than the remote control graphic user interface 1520*a*, a quick button 1520 may be displayed to provide channels viewed by the user often.

Alternatively, the wearable terminal 100 may send user information to a desk top computer 3 as the external device which can be used by user log-in so that the user can use the external device without an additional log-in process. A status bar 1512*a* showing a log-in status may be provided on the display unit 151.

Figure 19A:
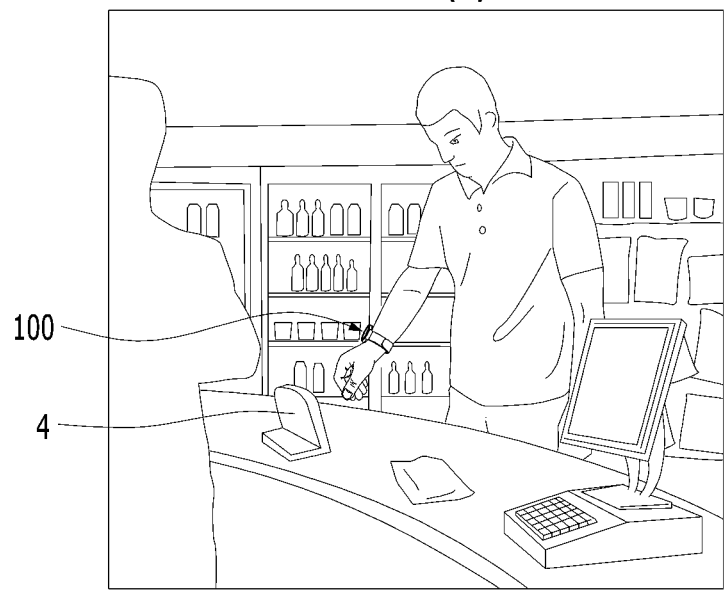
FIGS. 19(a) and 19(b) are diagrams illustrating personalized control for a user of the wearable terminal in accordance with the present disclosure.
Figure 19B:
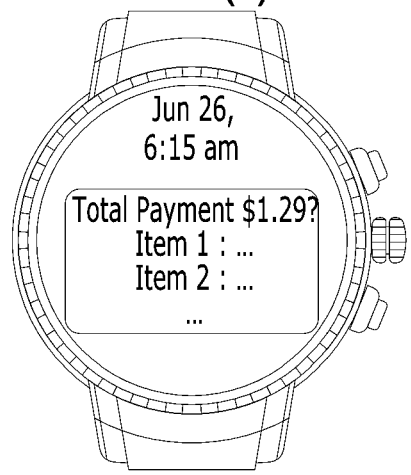

A mobile payment process requires user authentication as shown in FIG. 19. The user may input a personal identification number or a pattern and release a locked status to progress the payment process. The payment system may be used by a third person inputting the corresponding the personal identification number or the pattern equally. However, in case of using the ECG sensor 145, only the actual user can use the payment system. Accordingly, the user can progress the payment, without using additional authentication means such as an accredited certificate.

When the user approaches the wearable terminal 100 near a payment terminal as shown in FIG. 19(*a*), payment is implemented or processed without an auxiliary authentication process. After that, the details of the payment may be stored as shown in FIG. 19(*b*) and expenditures for each category may be checked, even without receipts. Also, the details of expenditures are arranged or listed to keep a household account book automatically or the user's consumption trend is analyzed and provided to the user.

Figure 20:
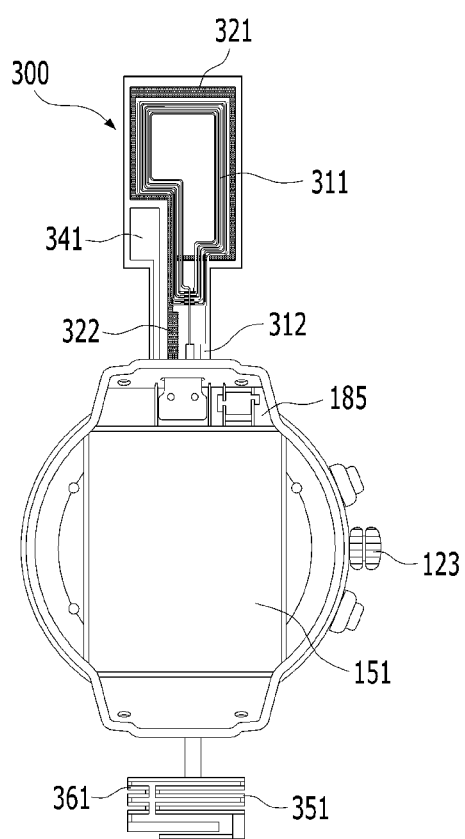
FIG. 20 is a diagram of antenna arrangement in the wearable terminal in accordance with one embodiment of the present disclosure.

FIG. 20 is a diagram of antenna arrangement in the wearable terminal in accordance with one embodiment of the present disclosure. A plurality of antennas may be mounted in the wearable terminal 100 to realize various functions.

Examples of the antennas mounted in the wearable terminal 100 may include a mobile communication antenna configured to permit long-range communication with a radio base station to make a call, send/receive a message and send data, a MIMO (Multiple-Input Multiple-Output) antenna configured to help the mobile communication antenna in case the mobile terminal antenna fails to function and to broaden a frequency band for mobile communication, a satellite antenna configured to receive a satellite signal, for example, GPS (Global Positioning System) signal, a DMB antenna configured to send/receive a large-capacity signal, for example, a DMB (Digital Multimedia Broadcasting) signal, a NFC (Near Field Communication) antenna configured to permit communication with a wireless device located in a short range, a WIFI antenna and a Bluetooth antenna.

As it is impossible to mount the plurality of the antennas in the main body 101, some of the antennas 310, 320, 341, 351 and 361 may be provided in the band 102. A pair of bands 102 are coupled to both sides of the main body 101 and it is possible to use the pair of the bands 102.

In this embodiment, a mobile communication antenna (not shown) is located in the main body 101 and a first MIMO antenna 311 which is a long-range antenna, a NFC antenna 311 which is a short-range antenna and a Bluetooth/WIFI antenna 341 are provided in an area next to the main body 101 (an upper area as illustrated). A second MIMO antenna 361 and a GPS antenna 351 are provided in the other area next to the main body 101 (a lower area as illustrated). The first MIMO antenna 321 and the NFC antenna 311 sends/receive signals in frequency bands different from each other.

Such arrangement of the antennas may be one of various examples and combination thereof may be applied. If there are more than three antennas collected together, mutual interference is likely to occur and performance of the antennas is likely to deteriorate. It is preferred that the antennas are scattered for three or more antennas to be integrated in one spot.

Figure 21:
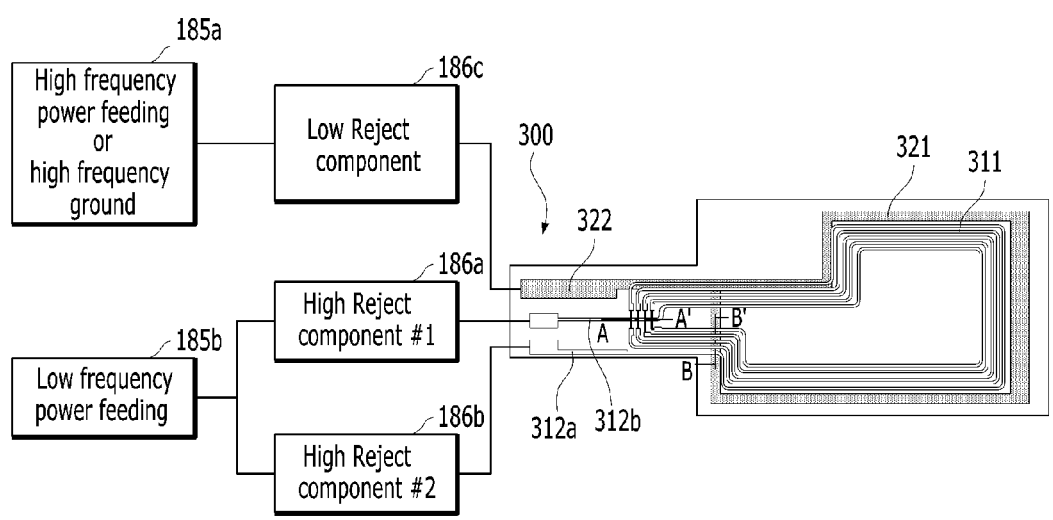
FIG. 21 is a diagram illustrating one embodiment of an antenna module provided in the wearable terminal in accordance with the present disclosure.
Figure 22:
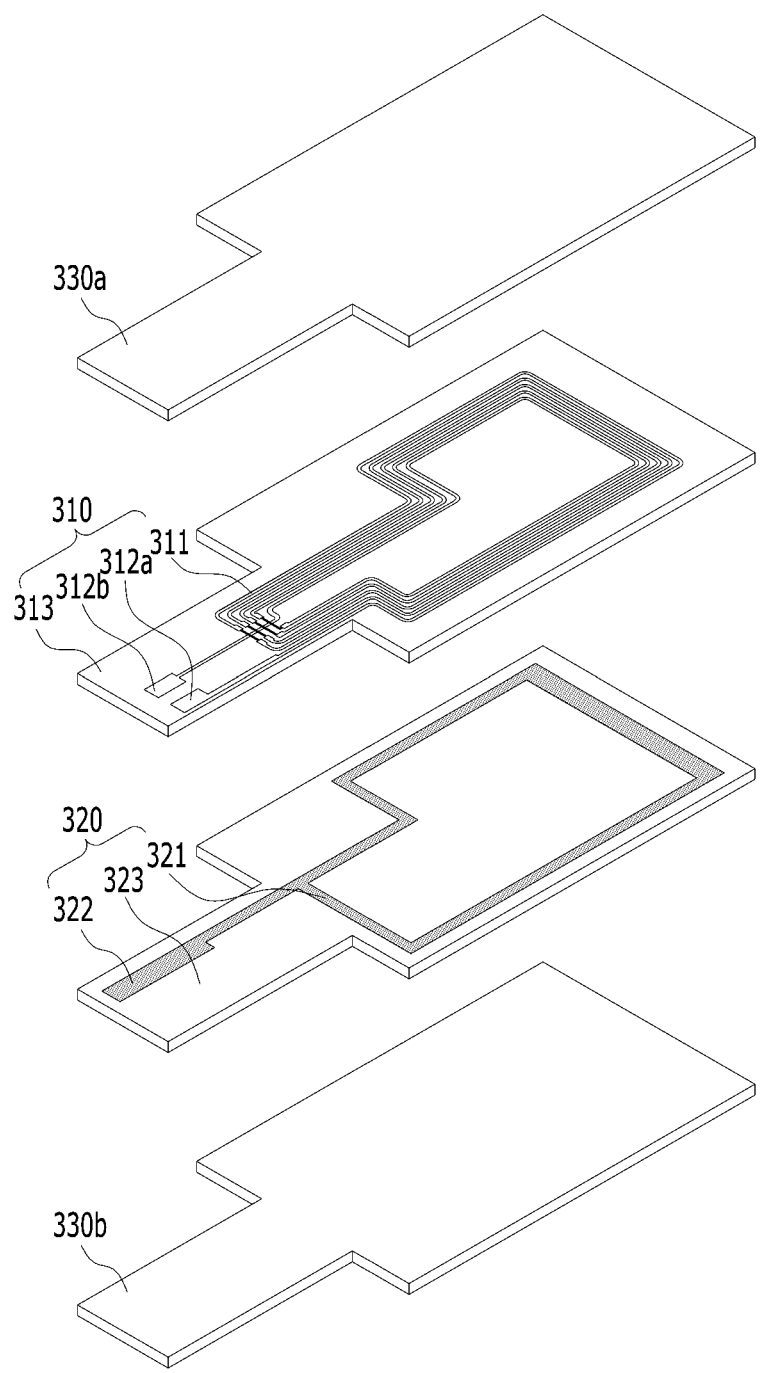
FIG. 22 is an exploded perspective diagram of FIG. 21.

FIG. 21 is a diagram illustrating one embodiment of an antenna module 300 provided in the wearable terminal 100 in accordance with the present disclosure. FIG. 22 is an exploded perspective diagram of FIG. 21.

The antenna module 300 mounted in a band 102 includes a first MIMO antenna and a NFC antenna. The first MIMO antenna is a high frequency antenna for long-range communication and the NFC antenna is a low frequency antenna for short-range communication. For description convenience sake, the NFC antenna is referenced to as the first antenna 310 and the first MIMO antenna is referenced to as the second antenna 320.

The first antenna 310 and the second antenna 320 shown in FIG. 22 are disposed in a layered structure. A protection film 330a and 330b may be disposed to protect an exposed surface of the first and second antennas 310 and 320. Each of the first and second antennas 310 and 320 may include a connection unit 312a, 312b and 322 configured to receive a power from a power feeding unit 185a and 185b and a radiation unit 311 and 321 configured to radiate an electromagnetic wave as currents flows from the connection unit 312a, 312b and 322. A frequency of the radiated signal may be variable according to the shape, length and area of the radiation unit 311 and 321.

The first antenna 310 may include a first insulation sheet 313 formed of a non-conductive material, a first radiation unit 311 formed in a surface of the first insulation sheet, with a spiral form, and a connection unit connecting a spiral end of the first radiation unit 311 to the main board 185. The connection unit includes a first connection unit 312a connected to one end located in an outer portion of the spiral form and a second connection unit 312b connected to one end located in the spiral form. The second connection unit 312b is extending from an internal end of the spiral form, to be overlapped with the first radiation unit 311 formed in the spiral shape.

Figure 23A:
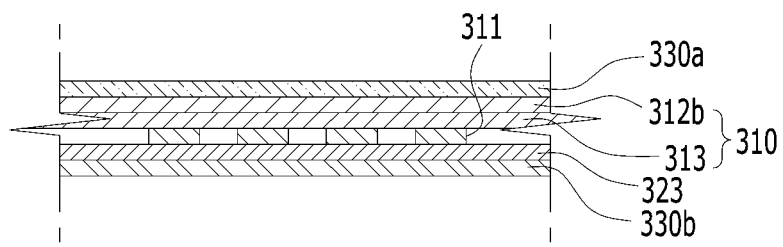
FIGS. 23(a) and 23(b) are sectional diagrams of A-A' and B-B' of FIG. 21.

To prevent the first radiation unit 311 and the second connection unit 312b from overlapping with each other, the second connection unit 312b is located in one surface and the first radiation unit 311 is located in the other surface. FIG. 23(a) is a sectional diagram of A-A' of FIG. 21. As illustrated, the second connection unit 312b is located in one surface of the first insulation sheet 313 provided in the first antenna 310 and the first radiation unit 311 is located in the other surface of the first insulation sheet 313.

The overall area of the first radiation unit 311 is located in the other surface. The second connection unit 312b and only an inner spiral end of the first radiation unit 311 are connected to each other through a via-hole penetrating the first insulation sheet 313. The overall area of the first radiation unit 311 is located in one surface of the insulation sheet, except the area overlapped with the second connection unit 312b located in the other surface.

The two types of the antennas 310 and 320 are implemented or operated in different frequency bands, respectively, so that performance efficient environments for the two antennas 310 and 320 are different from each other. Accordingly, the two types of the antennas might be interfered in each other in the area where the radiation units 311 and 321 are overlapped with each other.

When a conductive material, for example, metal is disposed near the antenna, eddy currents occur only to deteriorate the performance of the antenna. To suppress the eddy currents, a ferrite sheet may be disposed between the antenna and the conductive material located adjacent to each other.

The antenna is also formed of a conductive material. The ferrite sheet is disposed between the first antenna 310 and the second antenna 320 and mutual interference between the antennas is prevented, so that the eddy current generated by the overlapped arrangement of the antennas formed of the conductive material.

A conventional second antenna for long-range communication uses a plate-type radiation unit, so that there may be a large overlapped area between the first antenna disposed in the layered structure and the radiation unit enough to cause the eddy currents. Because of that, the ferrite sheet is used for the disadvantage mentioned above.

The ferrite sheet is an oxidized steel compound which is magnetic or activated in a magnetic field to be magnetized in the magnetic field and to cut off the magnetic field which affects the antenna. Especially, the ferrite sheet may be used so as to secure the performance of the low frequency antenna. In case of the high frequency antenna, a high frequency signal is affected by the ferrite sheet and the efficiency of the antenna can be deteriorated.

To solve such a problem, the first radiation unit 311 of the first antenna 310 and the second radiation unit 321 of the second antenna 320 are arranged not to be overlapped with each other, so that the mutual interference can be minimized to prevent the eddy current. Also, no ferrite is provided so that the performance of the second radiation unit 321 may be improved.

Figure 23B:
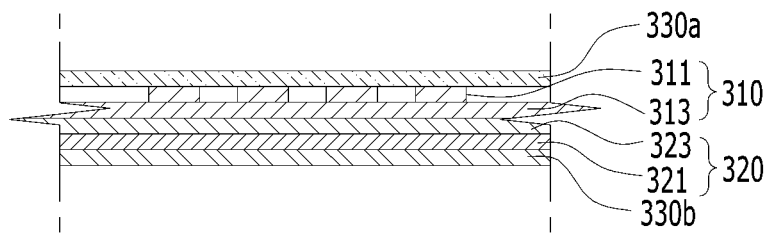

As shown in FIGS. 21 and 22, the first radiation unit 311 of the first antenna 310 in accordance with the present disclosure is arranged in a spiral form. The second radiation unit 321 of the second antenna 320 is formed in a loop form having no central area of the conventional plate-shaped radiation unit. The loop-shaped second radiation unit 321 is provided in an outer area of the first antenna. The second radiation unit 321 may have a partially overlapped area as shown in FIG. 21, because of space restriction. FIG. 23(b) is a sectional diagram of B-B' shown in FIG. 21. As illustrated, the first radiation unit 311 and the second radiation unit 321 may be overlapped vertically.

One or more of the first and second insulation sheets 313 and 323 may be disposed between the first radiation unit 311 and the second radiation unit 321, so that direct contact between the first and second radiation units may be prevented. The overlapped area between the first and second radiation units 311 and 321 is arranged an outer area from the spiral form of the first radiation unit 311 to occupy 25% or less of an overall area of the second radiation unit 321 and an overall area of the first radiation unit 311.

The shape of the second radiation unit 321 provided in the second antenna 320 is determined so as to secure all of the performance carried out by both of the first and second antennas 310 and 320 by minimizing the overlapped area with the first radiation unit 311, even without the ferrite sheet.

Figure 24A:
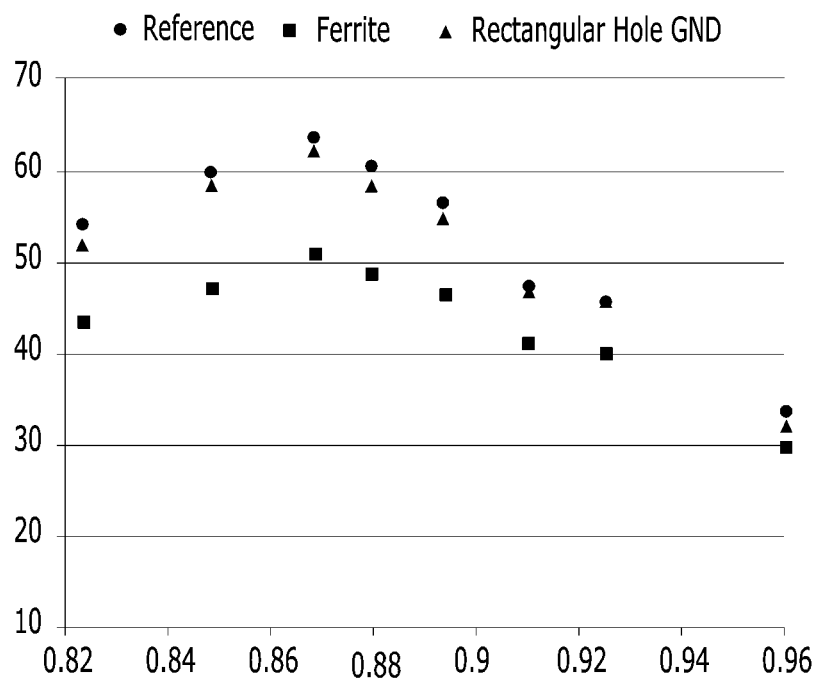
FIGS. 24(a) and 24(b) are graphs illustrating efficiency of a second radiation unit provided in the antenna module of the wearable terminal in accordance with the present disclosure.
Figure 24B:
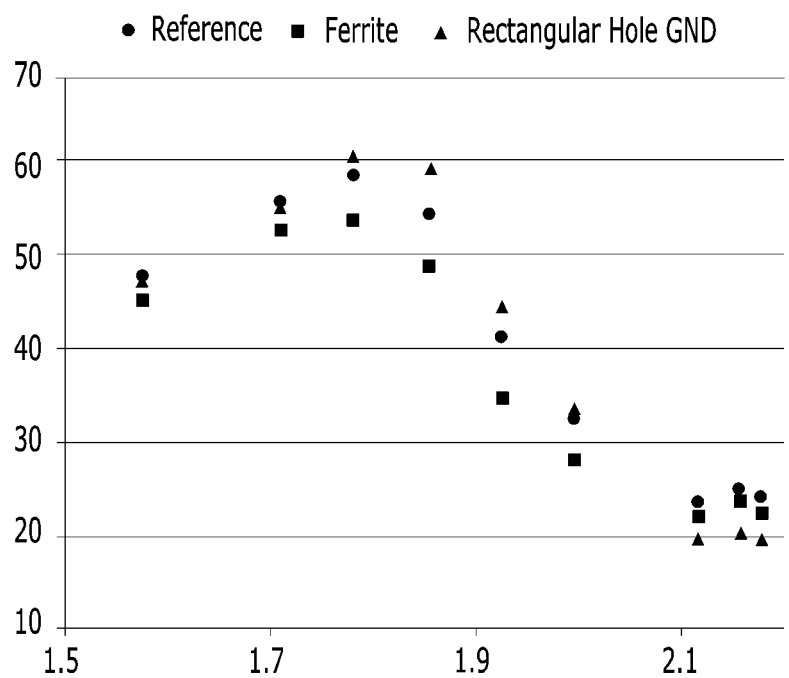

FIG. 24 is a graph illustrating efficiency of the second radiation unit 320 provided in the antenna module 300 of the wearable terminal 100 in accordance with the present disclosure. FIG. 24(a) shows efficiency in a frequency band between 820 MHz and 960 MHz and FIG. 24(b) shows efficiency in a frequency band between 1.5 GHz and 2.2 GHz.

A reference refers an efficiency value in a condition of one antenna with the plate-shaped radiation unit having a central portion of the loop-shaped second radiation unit 321 filled therein and the antenna has no affection of the other antenna. Ferrite refers to an efficiency value in a status where the antenna having the plate-shaped radiation unit is disposed in the layered structure and an efficiency value of the second antenna 320 having the loop-shaped second radiation unit 321 with an open central area in accordance with the embodiment.

A rectangular hole refers to the efficiency of the second antenna 320 formed in the loop shape having the hole shown in FIG. 21. Compared with the case having the ferrite sheet disposed between the radiation units, the efficiency of the loop-shaped second antenna is relatively high in most frequency bands and similar to the reference. The first MIMO antenna mainly sends/receives a signal in a frequency band from 700 MHz or more to 1.7 GHz or less so that the radio wave transmission and reception efficiency of the second antenna 320 in accordance with this embodiment is higher than the efficiency of the antenna having the auxiliary ferrite sheet in the frequency band.

Figure 25:
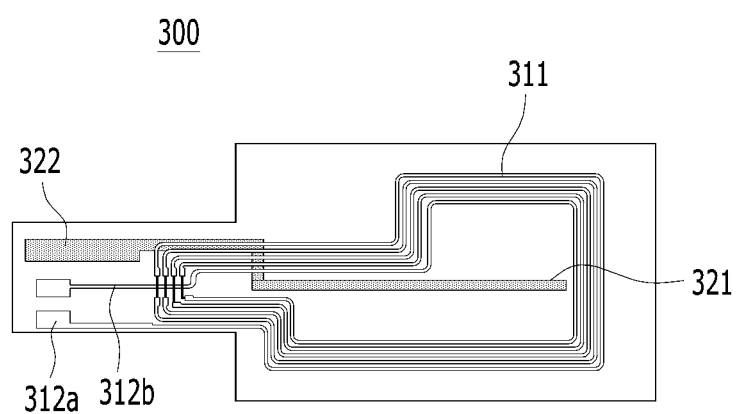
FIG. 25 is a diagram illustrating another embodiment of the antenna module provided in the wearable terminal in accordance with the present disclosure.

FIG. 25 is a diagram illustrating another embodiment of the antenna module 300 provided in the wearable terminal 100 in accordance with the present disclosure. The second radiation unit 321 may use a bar-shaped antenna rather than the loop-shaped antenna. Even in this embodiment, the overlapped area between the first and second radiation units 311 and 321 is determined to be 25% of less of the overall area of the second radiation unit 321 of the second antenna 320. An internal portion from the radial form of the first radiation unit 311 is an empty space and the second radiation unit 321 may be arranged in the space.

In spite of such the shape, the first and second radiation units might be interfered in each other. Accordingly, a low frequency reject module or a high frequency reject module may be provided between the connection unit of each antenna and the power feeding unit of the main board 185.

A high frequency reject module disposed between the connection unit of the first antenna and the power feeding unit may permit only a signal in a low frequency band to pass there through and a signal in a high frequency band not to pass there through. Examples of the high frequency wave removing module include one or more of a low pass filter configured to pass only the low frequency there through, a low band pass filter configured to pass only a signal corresponding to a frequency in a preset low frequency band there through, a high reject filter and a high reject filter configured to reflect a signal corresponding to a preset high frequency band.

The high frequency reject module may include one or more of combination of inductor and capacitor, a ceramic/dielectric filter, SAW (surface acoustic wave), MEMS (micro electro mechanical systems), LTCC (Low Temperature Co-firing Ceramics) and FBAR (Film Bulk Acoustic Resonator).

The low frequency reject module disposed between the connection unit of the second antenna 320 and the power feeding unit passes only the signal in the high frequency band and rejects the signal in the low frequency band. Examples of the low frequency removing module include one or more of a high pass filter configured to pass only the high frequency there through, a high band pass filter configured to pass only a signal corresponding to a frequency in a preset high frequency band there through, and a low reject filter configured to reflect a signal corresponding to a preset high frequency band.

The configuration of the low frequency reject module is similar to that of the high frequency reject module.

As mentioned above, when using the wearable terminal 100 including the ECG sensor 145 in accordance with at least one of the embodiments of the present disclosure, the user authentication may be facilitated easily with no auxiliary user identification means. Also, the wearable terminal 100 aiming for users may provide the user personalized function according to presence of user authentication.

In addition, the wearable terminal 100 may minimize the interference between the antennas overlapped with each other and reduce the material cost and thickness of the wearable terminal.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A wearable terminal comprising:
   a main body;
   a main board in the main body;
   a first touch pad coupled to a rear surface of the main body;
   a band coupled to the main body, the band configured to secure the wearable terminal to the user;
   a second touch pad positioned such that a user can touch the second touch pad when the wearable terminal is secured to the user's body;
   a conductive board connected to the second touch pad and to the main board; and
   a controller configured to measure a difference in electric potentials between the first touch pad and the second touch pad, and based on the measured difference in electric potentials, generate an electrocardiogram,
   wherein the band comprises:
   a lower band configured to contact the user's body; and
   an upper band coupled to the lower band, wherein the conductive board is made of a flexible material and mounted between the upper band and the lower band, and wherein the second touch pad is positioned on the upper band and connected to the flexible conductive board through a hole formed in the upper band.

2. The wearable terminal of claim 1 further comprising:
a conductive elastic material disposed between the second touch pad and the flexible conductive board to electrically connect the second touch pad and the flexible conductive board.

3. The wearable terminal of claim 1 further comprises a display unit,
wherein the controller controls the display unit to display a first screen when a difference in electric potential is sensed between the first touch pad and the second touch pad.

4. The wearable terminal of claim 1, wherein the controller measures the electrocardiogram and performs a user authentication by comparing the measured electrocardiogram with a designated user's preset electrocardiogram.

5. The wearable terminal of claim 4, wherein when the designated user's preset electrocardiogram matches the measured electrocardiogram, the controller performs one or more of implementing a function preset by the designated user, implementing a payment function, controlling an external device, implementing user authentication of an external device, and controlling a designated external device according to an input control command.

6. The wearable terminal of claim 4, wherein the user authentication is canceled when the first touch pad is released from user's body.

7. The wearable terminal of claim 4 further comprises a display unit,
wherein the controller controls the display unit to display a user authentication guide when user authentication fails, and wherein the controller controls the transmission of wearable terminal location information to a server when user authentication fails a preset number of times.

8. The wearable terminal of claim 4, wherein the controller controls the generation of an alarm when user authentication fails a preset number of times.

9. A wearable terminal comprising:
a main body;
a main board in the main body;
a first touch pad coupled to a rear surface of the main body;
a band coupled to the main body, the band configured to secure the wearable terminal to the user;
a second touch pad positioned such that a user can touch the second touch pad when the wearable terminal is secured to the user's body;
a conductive board connected to the second touch pad and to the main board; and
a controller configured to measure a difference in electric potentials between the first touch pad and the second touch pad, and based on the measured difference in electric potentials, generate an electrocardiogram,
an antenna module connected to the main board, wherein the antenna module comprises:
a first antenna comprising a first radiation unit having a spiral form; and
a second antenna disposed on the first antenna, the second antenna comprising a second radiation unit overlapping the first radiation unit, wherein the overlapping area constitutes 25% or less of the total area of the overlapping second antenna and the first radiation unit.

10. The wearable terminal of claim 9, wherein the first antenna further comprises:

a first insulation sheet, wherein the first radiation unit is formed on the first insulation sheet;
a first connection unit connected to and extending from an outer portion of the first radiation unit; and
a second connection unit connected to and extending from an inner portion of the first radiation unit, wherein the second connection unit partially provided on the other surfaces of the first insulation sheet for preventing overlap the first radiation unit, and wherein the first connection unit and the second connection units are electrically connected to the main board.

11. The wearable terminal of claim 10, wherein the main board comprises:
a power feeding unit connected to a power supply unit to supply power to the first radiation unit; and
a high frequency reject module disposed between the power feeding unit and one or both of the first and second connection units.

12. The wearable terminal of claim 11, wherein the high frequency reject module comprises one or more of a low pass filter configured to pass only low frequencies, a low band pass filter configured to pass only a preset low frequency signal, and a high reject filter configured to reflect a signal in a preset high frequency band.

13. The wearable terminal of claim 11, wherein the high frequency reject module comprises one or more of an inductor and a capacitor, a ceramic/dielectric filter, a SAW (surface acoustic wave) sensor, a MEMS (micro electromechanical system), an LTCC (low temperature co-firing ceramics) and a FBAR (film bulk acoustic resonator).

14. The wearable terminal of claim 11, wherein the second antenna comprises:
a second insulation sheet;
the second radiation unit formed on the second insulation sheet; and
a third connection unit connected to the second radiation unit, wherein the second radiation unit is formed in a loop shape or in a bar shape, wherein the second radiation unit partially overlaps the first radiation unit, and wherein the third connection unit is electrically connected to the main board.

15. The wearable terminal of claim 14, wherein the power feeding unit of the main board supplies power to the second radiation unit; and wherein the main board further comprises a low frequency reject module disposed between the power feeding unit and the third connection unit.

16. The wearable terminal of claim 15, wherein the low frequency reject module comprises one or more of a low pass filter configured to pass only low frequencies, a low band pass filter configured to pass only a preset low frequency signal a high reject filter configured to reflect a signal in a preset high frequency band.

17. The wearable terminal of claim 15, wherein the low frequency reject module comprises one or more of an inductor and a capacitor, a ceramic/dielectric filter, a SAW (surface acoustic wave), a MEMS (micro electro-mechanical system), an LTCC (low temperature co-firing ceramics) and a FBAR (film bulk acoustic resonator).

18. The wearable terminal of claim 9, wherein the first radiation unit is an NFC (Near Field Communication) antenna and the second radiation unit is a MIMO (Multiple Input Multiple Output) antenna.

19. The wearable terminal of claim 9 further comprising:
a band coupled to both ends of the main body and configured to secure the wearable terminal to a user's wrist, wherein an antenna module is mounted in the band and formed of a flexible material.

* * * * *